United States Patent [19]

Bagshaw et al.

[11] Patent Number: 5,712,091
[45] Date of Patent: Jan. 27, 1998

[54] METHOD OF SELECTING GENETICALLY SUPERIOR SHRIMP

[75] Inventors: Joseph C. Bagshaw, Holden; Michael A. Buckholt, Worcester, both of Mass.

[73] Assignee: Worcester Polytechnic Institute, Worcester, Mass.

[21] Appl. No.: 219,746

[22] Filed: Mar. 29, 1994

Related U.S. Application Data

[63] Continuation of Ser. No. 913,591, Jul. 14, 1992, abandoned.
[51] Int. Cl.$^6$ ................................................. C12Q 1/68
[52] U.S. Cl. ................................................. 435/6; 435/91.2
[58] Field of Search .................................... 435/6, 91.2

[56] References Cited

U.S. PATENT DOCUMENTS 4,683,195   7/1987   Mullis et al. ........................ 435/6
4,683,202   7/1987   Mullis ................................. 435/91

OTHER PUBLICATIONS

Palumbi et al., "Large mitochondrial DNA differences between morphologically similar Penaeid shrimp" *Chem Abstracts* 116:560 abstract No. 148640t (1992).

Sunden, "Population structures, evolutionary relationships and genetic effects of domestication in American Panaeid shrimp" *Chem. Abstracts* 118:490–491 abstract No. 121290h (1993).

Barringer, Kevin, J., et al., "Blunt–end and Single–strand Ligations by *Escherichia coli* Ligase: Influence on an In Vitro Amplification Scheme," *Gene*, 89:117–122 (1990).

Chu, Barbara, C.F., et al., "Synthesis of an Amplifiable Reporter RNA for Bioassays," *Nucleic Acids Research*, 14(14):5591–5603 (1986).

Compton, Teresa, "Degenerate Primers for DNA Amplification," *PCR Protocols: A Guide to Methods and Application*, 39–45 (Academic Press, Inc., New York, 1990).

Compton, J., "Nucleic Acid Sequence–based Amplification," *Nature*, 350(6313):91–92 (1991).

Graham, F.L., et al., "A New Technique for the Assay of Infectivity of Hyman Adenovirus 5 DNA," *Virology*, 52:456–467 (1973).

Haase, Ashley, T., et al., "Amplification and Detection of Lentiviral DNA Inside Cells," *Proc. Natl. Acad. Sci. USA*, 87:4971–4975 (1990).

Haase, Ashley, T., "Analysis of Viral Infections by In Situ Hybridization," *Oxford University Press. Chap.* 11, 197–219 (1987).

Haase, Ashley, T., et al., "Detection of Viral Nucleic Acids by in Situ Hybridization," *Methods in Virology*, vii:189–226 (1984).

Innis, Michael, A., et al., "PCR Protocols–A Guide to Methods and Applications," *Academic Press, Inc.*, 337–385 (1990).

Kimura, Genki, et al., "Isolation and Characterization of Temperature–Sensitive Mutants of Simian Virus 40," *Virology*, 49:394–403 (1972).

Kramer, F.R., et al., "Replicatable RNA Reporters," *Nature*, 339 (1989).

Kwoh, D.Y., et al., "Transcription–based Amplification System and Detection of Amplified Human Immunodeficiency Virus Type 1 with a Bead–based Sandwich Hybridization Format," *Proc. Natl. Acad. Sci. USA*, 86:1173–1177 (1989).

Landegren, Ulf, et al., "DNA Diagnostics –Molecular Techniques and Automation," *Science*, 242:229–237 (1988).

Landegren, Ulf, et al., "A Ligase–Mediated Gene Detection Technique," *Science*, 241:1077–1080 (1988).

Lizardi, Paul M., et al., "Exponential Amplification of Recombinant–RNA Hybridization Probes," *Biotechnology*, 6:1197–1202 (1988).

Loh, Elwyn Y., et al., "Polymerase Chain Reaction with Single–Sided Specificity: Analysis of T Cell Receptor & Chain," *Science*, 243:217–243 (1989).

Lomell, Hilda, et al., "Quantitative Assays Based on the Use of Replicatable Hybridization Probes," *Clin. Chem.*, 35(9):1826–1831 (1989).

Marx, Jean L., "Multiplying Genes by Leaps and Bounds," *Science*, 240:1408–1410 (1988).

Palumbi, Stephen, R., et al., "Large Mitochondrial DNA Differences Between Morphologically Similar Penaeid Shrimp," *Molecular Marine Biology and Biotechnology*, 1(1):27–34 (1991).

Potter, Huntington, et al., "Enhancer–dependent Expression of Human K Immunoglobulin Genes Introduced Into Mounse Pre-B Lymphocytes by Electroporation," *Proc. Natl. Acad. Sci. USA*, 81:7161–7165 (1984).

Renz Manfred, et al., "A Colorimetric Method for DNA Hybridization," *Nucleic Acids Research*, 12(8):3436–3444 (1984).

Sandri–Goldin, Rozanne M., et al., "High–Frequency Transfer of Cloned Herpes Simplex Virus Type 1 Sequences to Mammalian Cells by Protoplast Fusion," *Molecular and Cellular Biology*, 1(8):743–752 (1981).

(List continued on next page.)

*Primary Examiner*—Scott W. Houtteman
*Attorney, Agent, or Firm*—Arnall Golden & Gregory

[57] ABSTRACT

A method for the selection of shrimp having a genetically-transmitted favorable growth characteristic for improved aquacultured shrimp production. A genetic marker for the favorable characteristic is prepared by isolating Penaeus shrimp nuclear DNA by extraction with chloroform in the presence of cetyl trimethyl ammonium bromide, digesting the DNA with one or more restriction enzymes, and identifying characteristic restriction fragments. The marker is hybridized to a nuclear nucleic acid molecule isolated from Penaeus shrimp for the selection of shrimp having the desired characteristic. The marker can be a labelled probe or a primer for amplification and subsequent detection of a gene that encodes a protein promoting the desired growth characteristic. The selected shrimp can be used to produce a high quality, genetically superior seedstock or larvae useful for the economic production of aquacultured shrimp.

11 Claims, 8 Drawing Sheets

OTHER PUBLICATIONS

Sanger, F., et al., "DNA Sequencing With Chain-terminating Inhibitors," *Proc. Natl. Acad. Sci. USA*, 74(12):5463–5467 (1977).

Stoflet, E.S., et al., "Genomic Amplification with Transcript Sequencing," *Science*, 239:491–494 (1988).

Sompayrac, Lauren M., et al., "Efficient Infection of Monkey Cells with DNA of Simian Virus 40," *Proc. Natl. Acad. Sci. USA*, 78(12)7575–7578 (1981).

Vaughn, Jack C., et al., "Molecular Cloning and Characterization of Ribosomal RNA Genes from the Brine Shrimp," *Biochimica et Biophyisica Acta*, 697:156–161 (1982).

Wu, Dan Y., et al., "The Ligation Amplification Reaction (LAR) –Amplification of Specific DNA Sequences Using Sequential Rounds of Template-Dependent Ligation," *Genomics*, 4:560–569 (1989).

Andrews, M.T., "Organization of Histone Genes in Artemia," Doctoral Dissertation, Wayne State University, Detroit, MI (1984).

Kim et al., J. Crustacean Biol 10(1):1–13 1990 Abstract & 18S rRNA Nucleotide Sequences.

Steinbrück et al., Z Zool Syst Evolut –Forsch, 29:393–408, Dec. 1991.

Bradfield et al. Biol Bull (Woods Hule), 177(3):344–349, 1989 see Abstract, Biosis Data Bank Accession.

Ishaq et al., Biotechniqes 9(1):19–20,22,24 Jul. 1990.

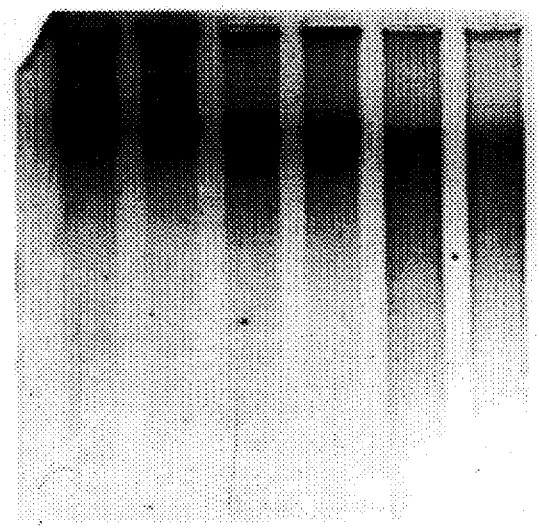

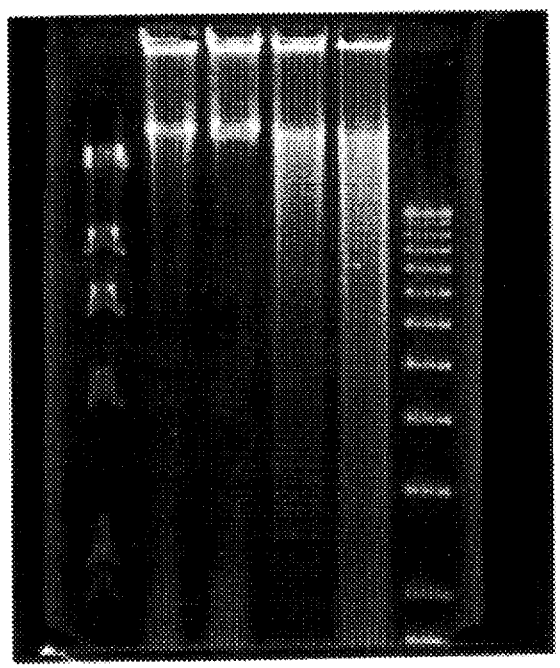

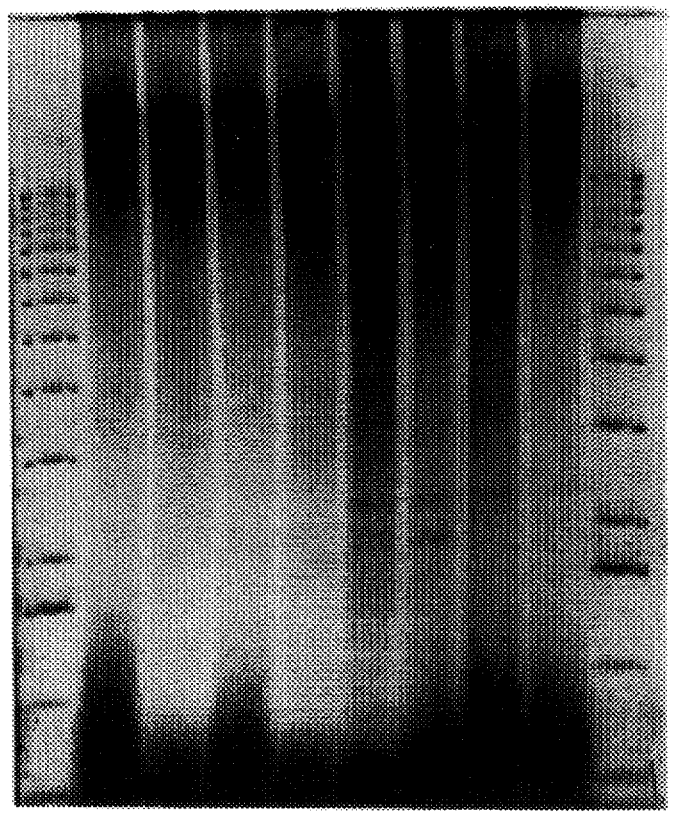

pBS r3

1 2 3 4

1 2 3 4

M 1 2 3 4 5

M 1 2

METHOD OF SELECTING GENETICALLY SUPERIOR SHRIMP

This is a continuation of application Ser. No. 07/913,591 filed on Jul. 14, 1992, now abandoned.

The United States government has rights in this invention by virtue of U.S. Department of Agriculture CSRS Grant Nos. 88-388083319 and 88-38808-3320.

BACKGROUND OF THE INVENTION

This relates generally to the field of shrimp farming and more particularly relates to the identification of nucleic acid sequences in shrimp.

Shrimp is a very popular seafood, highly favored for human consumption worldwide, especially in Japan and the United States. According to consumer surveys, shrimp dominates consumer preferences in all regions of the United States. The preferred species, *Penaeus vannamei*, lives only in warm water and can, therefore, be harvested in only limited areas of the world, including the southernmost region of the United States.

Shrimp farming, or agriculture, is the production of marine shrimp in impoundments, ponds and tanks. The requirement for a warm water environment has limited shrimp farming in the United States to a few locations in Florida, South Carolina, Texas and Hawaii with the result that only one hundredth of one percent of the annual U.S. shrimp consumption is supplied by these farms. Shrimp farms can be established on previously unused land, normally maintain a high yield, and avoid the environmental problems associated with the unintended capture and injury of marine wildlife, such as dolphins and turtles, in the shrimp trolling nets.

On a typical shrimp farm, juvenile shrimp are cultured at high densities in shrimp nurseries or small ponds, and, upon maturation, are transferred to a growout operation until they attain sufficient market-size for consumption. Juvenile shrimp are supplied from a shrimp hatchery or are captured from the wild.

In a shrimp hatchery, egg-laden females are spawned, and young shrimp are raised through several larval and post-larval stages. Hatcheries normally provide two types of juveniles for transfer to a nursery: nauplii (tiny, newly-hatched larvae) and post-larvae (juveniles that have passed through three larval stages; namely, nauplius, zoea, and mysis). The problems associated with shrimp hatcheries include disease and poor water quality. A disease-infested or polluted hatchery can cause illness or death of all or most of the larvae, resulting in the abrupt termination of juvenile shrimp production.

Disease represents the biggest obstacle to the future of shrimp farming. Farms and hatcheries have few defenses against protozoa, fungi and bacteria; and viral infections can be devastating. Viral infections have already contributed to shrimp crop failures throughout the world. No pharmaceutical products are currently available to treat shrimp viruses. When faced with a rampant vital infection, shrimp farmers are often forced to discard the entire crop, drain the ponds or tanks, disinfect the premises, and resupply the tanks with uninfected larvae or shrimp obtained from the wild or another hatchery.

Over the past few years, non-marine farmers have developed strains of poultry and livestock that are resistant to disease and exhibit enhanced growth rates or size. These strains are obtained by screening and breeding animals for the desired characteristics, thus optimizing production of genetically superior progeny. Shrimp farmers have not yet established strains of shrimp having such improved characteristics.

Mitochondrial DNA from several species of Penaeid shrimp have been sequenced by Palumbi and Benzie, *Mol. Marine Biol.* 1:27–34 (1991). A comparison of these sequences between morphologically similar species reveals a high degree of genetic divergence. Nuclear DNA from Penaeid shrimp has not yet been isolated or subjected to restriction fragment length polymorphism analysis.

The development of shrimp exhibiting superior characteristics such as disease resistance would enable shrimp farmers to hatch, grow and market increased quantities of high quality shrimp at a lower cost.

It is therefore an object of the present invention to provide a method for selecting shrimp having genetically-transmitted favorable characteristics such as disease resistance, enhanced growth rate, increased size, or the ability to grow in colder waters.

It is a further object of the present invention to provide a genetically engineered or transgenic shrimp.

It is a further object of the present invention to provide an economical method for producing shrimp.

SUMMARY OF THE INVENTION

A method is provided for the isolation of Penaeus shrimp nuclear DNA. Nuclear DNA is isolated from shrimp by chloroform extraction in the presence of cetyl trimethyl ammonium bromide. The isolated DNA is fragmented and used as a marker for the selection of shrimp having a genetically-transmitted favorable growth characteristic, such as increased reproduction, enhanced growth rate, increased size, disease-resistance, and the ability to grow in colder waters, for improved aquacultured shrimp production. The marker is either a genetic probe cloned from shrimp specific for a nucleic acid sequence associated with the desired characteristic or a genetic primer specific for a nucleic acid sequence flanking a gene, which encodes a protein that promotes the desired growth characteristic, for amplification and subsequent detection of the gene.

Hybridization of the marker to an isolated Penaeus shrimp nucleic acid molecule can be used to identify species, strains or individual shrimp having the desired characteristics. Once identified, these shrimp can be bred to shrimp having the same or an additional desired characteristic to produce a high quality, genetically superior seedstock or larvae useful for the economic production of farmed shrimp.

Recombinant or transgenic shrimp containing a nucleic acid sequence for a gene encoding a protein that promotes a favorable growth characteristic are also described.

BRIEF DESCRIPTION OF THE DRAWINGS

FIG. 1A is an agarose gel electrophoresis of undigested (lanes 1–4) and EcoRI-digested (lanes 5–6) DNA from post-larvae (lanes 1, 3, and 5) and tail muscle (lanes 2, 4, and 6) Penaeus shrimp.

FIG. 1B is an agarose gel electrophoresis of DNA from post-larvae Penaeus shrimp digested with BamHI (lanes 1 and 3) or EcoRI (lanes 2 and 4) either before (lanes 1 and 2) or after (lanes 3 and 4) chloroform extraction in the presence of cetyl trimethyl ammonium bromide. The lanes labelled "M" are markers.

FIG. 2A is an agarose gel electrophoresis of DNA isolated from post-larvae Penaeus shrimp after digestion with BamHI (lane 1), ClaI (lane 2), EagI (lane 3), EcoRI (lane 4), HindIII (lane 5), KpnI (lane 6) PstI (lane 7), and XbaI (lane 8). The lanes labelled "M" are markers.

DETAILED DESCRIPTION OF THE INVENTION

Figure 2B:
FIG. 2B is a Southern blot of the electrophoretic gel of FIG. 2A hybridized with pBSr3, a plasmid containing the 5.8 S rRNA gene, part of the 28 S rRNA gene and part of the internal transcribed spacer from Artemia shrimp.

A genetic method is provided for the selection of shrimp having one or more favorable growth characteristics. In accordance with the method, DNA is extracted from Penaeus shrimp and is digested with one or more restriction enzymes for identification and subsequent cloning of a marker specific for a Penaeus shrimp nucleic acid sequence associated with or comprising a gene or genes conferring the favorable growth characteristic. The marker is hybridized to an isolated shrimp nucleic acid molecule, such as DNA or RNA, for detection of the sequence of interest using well known hybridization techniques as described by Sambrook, Frisch & Maniatis, *Molecular Cloning: A Laboratory Manual*, 2nd Ed., (Cold Spring Harbor Laboratory, N.Y. 1989), the teachings of which are incorporated herein by reference. Shrimp species, strains or individual shrimp having a nucleic acid molecule that hybridizes to the marker will have the favorable growth characteristics and can be bred to shrimp having the same or an additional favorable characteristic to produce genetically superior seedstock or larvae useful for the economic production of aquacultured shrimp.

In addition, shrimp can be genetically manipulated to insert nucleic acid sequences containing a gene or genes from shrimp, other organisms, or synthetic DNA that confer favorable growth characteristics, into the shrimp nuclear genome to create recombinant or transgenic shrimp.

Favorable growth characteristics include, but are not limited to, increased reproduction, enhanced growth rate, increased size, disease-resistance, and the ability to grow in colder waters. Genes conferring favorable growth characteristics include, but are not limited to, homeotic genes, genes encoding transcription factors, genes encoding peptide hormones and their receptors, genes encoding digestive and other metabolic enzymes, genes encoding major structural proteins such as collagen, myosin, and actin, and genes encoding components of exoskeleton and its construction such as chitin synthase.

The marker can be either a nucleic acid probe, labelled with a detectable label for detection of the sequence of interest, or a nucleic acid primer specific for amplification of a nucleic acid sequence or sequences conferring the favorable characteristics. Preferably, amplification is achieved by utilizing the polymerase chain reaction, or variations thereof, in combination with two primers that hybridize to nucleic acid sequences flanking the sequence to be amplified for subsequent detection.

The term "shrimp" is defined herein as shrimp eggs, shrimp larvae, shrimp post-larvae and adult shrimp. The shrimp are preferably Penaeus shrimp and include the species *Penaeus vannamei*, *Penaeus chinensis*, *Penaeus monodon*, *Penaeus stylirostris*, *Penaeus japonicus*, *Penaeus penicillatus*, *Penaeus merguiensis*, *Penaeus indicus*, *Penaeus subtilis*, *Penaeus paulensis*, *Penaeus setiferus*, *Penaeus brasiliensis*, *Penaeus duorarum*, *Penaeus occidentalis*, *Penaeus schmitti*, *Penaeus californiensis*, *Penaeus semisulcatus*, *Penaeus latisulcatus*, *Metapenaeus monoceros*, *Metapenaeus dobsoni*, *Metapenaeus affinis*, and *Metapenaeus brivicornis*.

The term "marker" is defined herein as a nucleic acid sequence (DNA or RNA) that hybridizes to a genetically similar nucleic acid sequence (DNA or RNA) under standard hybridization conditions and includes probes and primers. Standard hybridization conditions are defined herein as hybridization at a temperature approximately 20°–40° C. or more below the melting temperature of a perfectly base-paired double stranded DNA molecule. The melting temperature of a double stranded DNA molecule can be determined by methods well known to those skilled in the art.

The marker is originally identified by first obtaining samples of a species, strain or individual shrimp having the favorable growth characteristic or characteristic, isolating high molecular weight DNA capable of restriction enzyme digestion from this sample by extraction with chloroform in the presence of cetyl trimethyl ammonium bromide, digesting the DNA with one or more restriction enzymes, separating the fragments on agarose gels by electrophoretic techniques, preparing Southern blots for hybridization, and cloning each fragment into a vector to prepare a DNA library. Clones from the gene library are tested by gel electrophoresis for the presence of characteristic patterns such as variable number of tandem repeats, dispersed repeats, and restriction fragment length polymorphisms. Promising clones can be sequenced to provide confirmation of repeat or polymorphic regions or further information pertaining to the characteristic pattern.

Isolation of Penaeus Nuclear DNA

Nucleic acid molecules, such as DNA or RNA, are isolated from fresh or frozen shrimp samples by extraction with chloroform in the presence of cetyl trimethyl ammonium bromide or a similar cetyl-containing organic compound. Use of standard DNA isolation procedures known to those skilled in the art failed to produce high molecular weight nucleic acid molecules useful for restriction enzyme digestion, two requirements necessary for the isolation of nucleic acid markers. High molecular weight nucleic molecules are defined herein as molecules having a length of 50,000 bases or greater.

For example, the DNA isolation method described by Andrew, M. T., "Organization of Histone Genes in Artemia", Doctoral Dissertation, Wayne State University, Detroit, Mich. (1984), that had been shown to provide excellent yield of genomic DNA from nauplius larvae of *Artemia franciscana*, was unsuccessful for the preparation of genomic DNA from *Penaeus vannamei*. Penaeus DNA degraded during the procedure, producing low molecular weight fragments that were not of the quality needed for DNA fingerprinting by the Southern blot approach. The method described in *Current Protocols in Molecular Biology* (John Wiley and Sons, 1987), for extracting DNA directly from ground whole animals without intervening isolation of nuclei, produced very high molecular weight DNA but was very tedious and time-consuming and not well suited to isolation and analysis of DNA from multiple samples. As described in an example below and shown in FIG. 7, the A.S.A.P.™ kit (Boehringer Mannheim, Indianapolis, Ind.) for rapid extraction of DNA by a gel matrix method, yielded badly fragmented DNA of no value. The Autoextract™ system (Isogene Biotechnology, Inc. Overland Park, Kans.) was better than the previously described standard methods, but still resulted in undesirable fragmentation of Penaeus DNA as described in an example below and shown in FIG. 6. Therefore, a DNA extraction method, specific for the isolation of high molecular weight DNA from Penaeus shrimp, was developed. The method is described below.

Penaeus DNA Extraction Method

A sample of frozen, post-larvae shrimp provided by the Oceanic Institute, Honolulu, Hi. was pulverized while frozen on dry ice. Two grams of the mixed powder was dropped directly into a prewarmed (50° C.) lysis buffer containing 50 mM tris(hydroxymethyl)aminomethane (Tris), pH 8 (Sigma Chemical Co. St. Louis, Mo.); 100 mM EDTA (Sigma), 1% sodium dodecyl sulfate (Pierce Chemical Company, Rockford, Ill.), and 100 μg/ml proteinase K (16 units/mg, Sigma Chemical Co.). The mixture was digested overnight at 50° C. and was extracted twice with a phenol and chloroform mixture (a ratio of 1:1 by volume) both obtained from International Biotechnologies, Inc., New Haven, Conn.; extracted once with 100% chloroform; the aqueous phase was dialyzed against a Tris/EDTA buffer containing 10 mM Tris(Sigma), pH 7.5, and 1 mM EDTA; adjusted to 0.7M NaCl, 1% (w/v) cetyl trimethyl ammonium bromide (CTAB, obtained from Kodak, Rochester, N.Y.); and extracted twice with chloroform. After the addition of isopropanol (Mallinckrodt Specialty Chemical Co., Paris, Ky.), the DNA was spooled out, rinsed in 70% ethanol (Aaper Alcohol and Chemical Co., Shelbyville, Ky.), and dissolved in the Tris/EDTA buffer.

DNA was also isolated from the finely minced tail muscle of a fresh *Penaeus vannamei* adult shrimp by the same procedure.

The DNA isolated from both samples was high in molecular weight and capable of being digested with restriction enzymes as shown in FIGS. 1A and 1B and demonstrated below in several of the examples.

Construction of Genomic DNA library

A library of genomic DNA was constructed by digesting the isolated nucleic acid molecule from Penaeus with one or more restriction enzymes, which were obtained from International Biotechnologies, Inc. (New Haven, Conn.) or New England Biolabs (Beverly, Mass.) and inserting size-selected restriction fragments, approximately 15,000 bases in length or less, into a suitable vector, such as lambda DASH™, lambda ZAP™, and pBluescript™, all available from Stratagene (La Jolla, Calif.), by methods known to those skilled in the art and described in detail by Sambrook, Frisch & Maniatis, *Molecular Cloning: A Laboratory Manual*, 2nd Ed., (Cold Spring Harbor Laboratory, N.Y. 1989), the teachings of which have been incorporated herein by reference. Construction of such a library is a standard first step in initiating molecular genetic studies, and provides one possible source of probes for the present shrimp selection method. The genomic gene library is useful for isolating clones of specific genes as well as other DNA sequences associated with favorable growth characteristics, such as sequences highly repeated in the genome.

For example, from the genomic DNA library, one can isolate clones of the genes encoding the major nucleolar ribosomal RNAs. The ribosomal RNA genes are useful for identifying particular species, strains or individual shrimp because these often contain polymorphisms that can be detected by either DNA hybridization probe techniques or polymerase chain reaction techniques that can be applied directly to ribosomal RNA (rRNA). Isolation of rRNA is simpler than isolation of DNA, can be readily automated, and can be performed on relatively small samples of tissue, such as the muscle tissue of a single leg.

Construction of cDNA Library

A cDNA gene library constructed by digesting complementary DNA, prepared from RNA incubation with reverse transcriptase, is useful for the isolation and characterization of specific protein-coding genes, such as, for example, those encoding neuropeptide hormones. Polyadenylated mRNA is isolated by selection on oligo-dT cellulose. Construction of the cDNA library can be carried out by one of the commercial suppliers of this service such as Invitrogen (San Diego Calif.), resulting in a library of cloned DNAs inserted into plasmid vectors.

Preparation of Penaeus Markers

A nucleic acid sequence marker is prepared from the genomic or cDNA library or by digestion of isolated high molecular weight shrimp DNA with one or more restriction enzymes into fragments approximately 15,000 bases or less as described above. The marker is preferably 20 bases in length or longer and can be a nucleic acid probe specific for a particular gene, specific for a restriction fragment length polymorphism, specific for variable number tandem repeats, specific for dispersed repeated DNA sequences, or the probe can be a specific for a gene or gene sequence flanking a gene.

The isolated fragment can then be cloned into a vector, such as lambda DASH™, lambda ZAP™, and pBluescript™ (all available from Stratagene, La Jolla, Calif.) and sequenced. Fragments cloned into plasmid vectors can be sequenced directly whereas clones in phage vectors generally must be sub-cloned into plasmid vectors before sequencing. The sequence of an isolated DNA fragment can be determined by the dideoxy chain termination method of Sanger et al., *Proc. Natl. Acad. Sci.* USA 74:5463–5467 (1977), using a Sequenase™ kit (U.S. Biochemical Corp., Cleveland, Ohio) according to the manufacturer's instructions or by other methods known to those skilled in the art. Once the sequence is known, a specified polynucleotide marker can be synthesized either in a biological system or in a chemical reaction in vitro in accordance with methods well known to those skilled in the art. Biological systems include both prokaryotic organisms such as bacteria and eukaryotic organisms such as yeast, isolated cells in culture, germ line cells in multicellular organisms, somatic tissue cells in multicellular organisms, or plant cells.

Molecular Genetic Probes

An isolated fragment or synthetic nucleic acid sequence capable of hybridization to isolated shrimp nucleic acid sequences associated with favorable growth characteristics can be labelled and used as a probe to select shrimp having the desired characteristics Preferred fragments are derived from regions of the Penaeus genome that contain the genes that confer desireable growth characteristic on the species, strain or individual shrimp. Fragments derived from regions exhibiting restriction fragment length polymorphisms, variable number tandem repeats, and dispersed repeats should exhibit enhanced specificity for the desired characteristics and be useful as probes.

The probes may be labelled with an atom or inorganic radical, most preferably using radionucleotides, such as $^{32}P$, $^{3}H$, $^{14}C$, $^{35}S$, $^{125}I$, $^{131}I$, or heavy metals. A $^{32}p$ label can be incorporated into the sequence of the probe by nick-translation, end-labelling or incorporation of a labelled nucleotide. A $^{3}H$, $^{14}C$ or $^{35}S$ label can be incorporated into the sequence of the probe by incorporation of a labelled precursor or by chemical modification. An $^{125}I$ or $^{131}I$ label can be incorporated into the sequence of the probe by chemical modification. Detection of a label can be by methods such as scintillation counting, gamma ray spectrometry or autoradiography.

The label can also be a Mass or Nuclear Magnetic Resonance (NMR) label such as, for example, $^{13}C$, $^{15}N$, or $^{19}O$. Detection of such a label can be by Mass Spectrometry or NMR.

Preferably the label is attached to the probe by chemical conjugation. Any label may be used that provides an adequate signal and has a sufficiently long half-life. Other preferred labels include dyes, ligands, fluorescers, chemiluminescers, enzymes, antibodies and similar compounds. For example, biotin can be bound to the probe and detected by binding an avidin-conjugated enzyme or streptavidin conjugated enzyme to the biotin followed by washing to remove non-specifically bound enzyme. Upon addition of an appropriate substrate for the enzyme, the substrate is converted to a colored or chemiluminescent product that can be detected. Examples of such enzymes include alkaline phosphatase and horseradish peroxidase as described by Renz et al., Nuc. Acids Res. 12:3435–3444 (1984). Examples of dyes include ethidium bromide, actidines, propidium and other intercalating dyes, and 4',6'-diamidino-2-phenylindole (DAPI)(Sigma Chemical Company, St. Louis, Mo.) or other proprietary nucleic acid stains. Examples of fluorogens include fluorescein and derivatives, phycoerythrin, allophycocyanin, phycocyanin, rhodamine, Texas Red or other proprietary fluorogens. The fluorogens are generally attached by chemical modification. The dye labels can be detected by a spectrophotometer and the fluorogens can be detected by a fluorescence detector.

Recognition sites for enzymes, such as restriction enzyme sites, can also be incorporated into the probes to provide a detectable label. A label can also be made by incorporating any modified base or precursor containing any label, incorporation of a modified base containing a chemical group recognizable by specific antibodies, or by detecting any bound antibody complex by various means including immunofluorescence or immuno-enzymatic reactions. Such labels can be detected using enzyme-linked immunoassays (ELISA) or by detecting a color change with the aid of a spectrophotometer.

The labelled probe can be hybridized to DNA or mRNA in cells in intact tissues or a sample containing fresh or frozen shrimp cells. Hybridization can be in vitro or in situ. The method of in situ hybridization is described by Haase, A., et al. "Detection of viral nucleic acids by in situ hybridization", In: *Methods in Virology* (Eds. K. Maramorosch & H. Koprowski) Vol. 7, pp.189–226, Academic Press, New York, 1984, which is incorporated by reference herein and Haase, A. T., et al., "Analysis of viral infections by in situ hybridization", In: *In situ Hybridization—Applications to Neurobiology* (Eds. K. Valentine, J. Roberts & J. Barchas), pp. 197–219, Oxford University Press [Symposium Monograph], Fairlawn, N.J., 1986, which is also incorporated by reference herein.

The method for determining the presence and quantity of a specific label depends on the label employed. Such methods are well known to those skilled in the art.

It will be understood by those skilled in the art that other labels can also be used. A review of nucleic acid labels can be found in the article by Landegren, et al., "DNA Diagnostics-Molecular Techniques and Automation". *Science*, 242:229–237 (1988) which is incorporated herein by reference.

Amplification of Penaeus Genomic DNA

The polymerase chain reaction (PCR) technique, described in U.S. Pat. Nos. 4,683,195 and 4,683,202 to Mullis, the teachings of which are incorporated herein by reference, can be used to amplify a specific sequence form vanishingly small samples of DNA or RNA to produce easily visualized DNA fragments of characteristic size. PCR, using either specifically defined or random primers, can therefore be used to identify species, strains and individual shrimp and to investigate population polymorphisms.

PCR technology is described in *PCR Protocols A Guide to Methods and Applications* by Michael A. Innis, David H. Gelfand, John J. Sninsky and Thomas J. White, pp. 39–45 and 337–385 (Academic Press, Inc., Harcourt Brace Jovanovich, Publishers, 1990), the teachings of which are incorporated by reference herein. PCR technology is also described by Marx, J. L., *Science* 140:1408–1410 (1988) and in U.S. Pat. Nos. 4,683,195 and 4,683,202, to Mullis, the teachings of which are also incorporated herein by reference.

PCR using one primer is described by Loh, E. Y., et al., *Science* 243:217 (1989), the teachings of which are incorporated herein by reference. This technique is often used with cDNA (DNA derived from messenger RNA by reverse transcriptase). There are also asymmetric PCR systems and other methods that use one primer or vast excess of one primer. These methods generate mostly single-stranded DNA, suitable for direct sequencing. Single primers can also be used with random hexamers (a degenerate mixture of all or most of the possible DNA hexamers) so that at least one hexamer will act as a second primer by hybridizing somewhere along the sequence at a distance from the first primer.

PCR technology requires pairs of dissimilar DNA oligo-nucleotides (short fragments of DNA sequence) which act as primers to initiate a controlled polymerase reaction which, in turn, amplifies the genomic sequence that lies between the two oligonucleotide binding sites. The polymerase chain reaction employs a heat-stable polymerase (the Taq polymerase) which permits repeated heating and cooling of the reaction mixture. The amplification process is initiated by first heating the reaction mixture to denature (dissociate) the two complementary strands of the double stranded DNA to be amplified. Upon cooling, each single-stranded DNA oligonucleotide hybridizes to a specific region of one or the other of the complementary DNA strands, and acts as a primer for the heat-stable polymerase. The polymerase uses the oligonucleotide primers as starting points for the elongation of a DNA molecule complementary to the template DNA molecule to which each primer is hybridized. Each of the elongating DNA chains grows towards and beyond the distal primer site of the other template strand. By the end of the first cycle two double stranded copies of the intervening genomic sequence lying between the primer binding sites are generated. The cycle is repeated manyfold, exponentially doubling the number of copies each time. In this fashion even a single copy of a specific DNA sequence can be amplified to detectable levels in a relatively short period of time.

The polymerase chain reaction primer selection is limited by three factors. First, the two oligonucleotides must be complementary to sequences found in the template DNA in order for the oligonucleotides to hybridize to the template DNA. Without this initial hybridization step there would be no primer available for the DNA polymerase to use to initiate elongation, and no copy of the DNA sequence could be made. Second, the primers should hybridize to discrete and unique regions of the template DNA. If the primers hybridize to multiple different sites in the template sequence then the initiation site for elongation, and the DNA copy produced, would vary from cycle to cycle depending upon to which binding site the primer hybridized. Third, the two primer binding sites must not be too distant from one another. The elongation step optimally produces fragments up to approximately 2500 bases in length, and DNA sequences of greater length are amplified less efficiently or not at all. If chain elongation terminates before the distal primer site is incorporated into the sequence, the resultant incomplete DNA molecule will not participate in subsequent rounds of amplification.

Examples of other applicable amplification systems that currently exist or are being developed include PCR in situ, ligase amplification reaction (LAR), ligase hybridization, Qβ bacteriophage replicase, transcription-based amplification system (TAS), genomic amplification with transcript sequencing (GAWTS) and nucleic acid sequence-based amplification (NASBA).

PCR in situ is the use of PCR amplification on cells or tissue sections followed by detection using in situ hybridization. This technique is described by Haase, A. T., et al., "Amplification and detection of lentiviral DNA inside cells", *Proc. Natl. Acad. Sci.* (USA) 87:4971–4975 (July 1990).

Ligase amplification reaction is described by Wu, D. Y. and Wallace, R. B., *Genomics* 4:560–569 (1989) and Barringer, K. J., et al., *Gene* 89:117–122 (1990), the teachings of which are incorporated herein by reference. Ligase hybridization is described by Landegren, U., et al., *Science* 241:1077–1080 (1988), the teachings of which are incorporated herein by reference.

The Qβ bacteriophage replicase system is described by Kramer, F. R. and Lizardi, P. M., "Replicatable RNA reporters", *Nature* 339:401–402 (1989); Lizardi, P. M., et al., "Exponential amplification of recombinant-RNA hybridization probes", *Bio/Technology* 6:1197–1202 (1988); Lomeli, H., et al., "Quantitative assays based on the use of replicatable hybridization probes", *Clin. Chem.* 35:1826–1831 (1989); and Chu, B. C. F., et al., *Nucl. Acids Res.* 14:5591–5603 (1986), the teachings of which are incorporated herein by reference.

TAS is described by Kwoh, D. Y., et al., *Proc. Natl. Acad. Sci. USA* 86:1173–1177 (1989), the teachings of which are incorporated herein by reference. GAWTS is described by Stoflet, E. S., et al., *Science* 239:491–494 (1988), the teachings of which are incorporated herein by reference. NASBA is described by Compton, J., *Nature* 350:91–92 (1991), the teachings of which are incorporated herein by reference.

Detection and analysis of the nucleotide fragments, amplified by one of the methods described above, are accomplished by standard methods including, for example, gel electrophoresis, dot blots, slot blots and colorimetry, as described in standard laboratory textbooks such as Sambrook, Frisch & Maniatis, *Molecular Cloning: A Laboratory Manual*, 2nd Ed., (Cold Spring Harbor Laboratory, N.Y. 1989), the teachings of which have been incorporated herein by reference.

Mutants

Once identified, nucleic acid sequences specific for favorable growth characteristics can be mutated by standard procedures, such as site-directed mutagenesis or electromagnetic irradiation, and mutants screened for improved growth characteristics. In this way, mutant shrimp having enhanced growth characteristic can be propagated to produce improved shrimp strains. For example, for isolation of a mutant, a phosphorylated oligonucleotide primer is synthesized so that it contains a mutation in the corresponding region of the shrimp genome. This first primer and a second oligonucleotide primer, without the mutation, is hybridized in solution to a single-stranded, circular plasmid construct containing a cDNA sequence complementary to the first primer and containing vector sequences complementary to the second primer. By the addition of a DNA polymerase lacking editing activity, the oligonucleotides prime the synthesis of an extended mutant DNA sequence using the vector/nucleic acid single strand as a template. Both primers are extended to where they meet and ligase is added to anneal them. This results in double-stranded particles that can be transformed into *E. coli* to allow for subsequent identification of mutated cDNAs through hybridizations with the mutagenic primer.

A modified protein expressed by a mutant shrimp gene having modified activity can be assessed by transfecting COS cells with the mutated cDNA in an expression vector and assaying the protein produced by the COS cells by a biochemical assay specific for enzyme activity. Such a mutant gene could be used as a probe for the identification of mutant shrimp or recombined into shrimp cells as described below for the creation of recombinant or transgenic shrimp.

Transgenic Shrimp

Genes from shrimp, other organisms such as lobster, or synthetic DNA, conferring favorable growth characteristics can be inserted into the genome of shrimp by one of several standard published procedures to form stable transformants, including, for example, calcium phosphate precipitation, DEAE-Dextran, electroporation, and protoplast fusion. These methods are described in detail as follows:

Calcium phosphate precipitation: DNAs are coprecipitated with calcium phosphate, according to the method of Graham and VanDer in *Virology* 52:456 (1973), before transfer into cells. 40–50 µg of DNA with salmon sperm or calf thymus DNA as carrier is used for 0.5×10⁶ cells plated on a 100 mm dish. DNA is mixed with 0.5 ml of 2× Hepes solution (280 mM NaCl, 50 mM Hepes and 1.5 mM Na$_2$HPO$_4$, pH 7.0) to which an equal volume of 2× CaCl$_2$ (250 mM CaCl$_2$ and 10 mM Hepes, pH 7.0) is added. A white granular precipitate appearing after 30–40 minutes is distributed dropwise evenly on the cells and allowed to sit for 4–16 hours at 37° C. The medium is removed and the cells are shocked with 15% glycerol in PBS for 3 minutes. After removing the glycerol, the cells are fed with Dulbecco's Minimal Essential Medium (DMEM) containing 10% fetal bovine serum and left in the incubator.

Protein samples are prepared for Western blot analysis by lysing cells and separating the proteins by SDS-PAGE. The proteins are transferred to nitrocellulose by electroblotting as described in *Current Protocols in Molecular Biology* (John Wiley and Sons, 1987). After blocking the filter with instant nonfat dry milk (1 g in 100 ml PBS), primary antibody is added to the filter and incubated for i hour at room temperature. The filter is washed thoroughly with phosphate buffered saline (PBS) and incubated with horseradish peroxidase (HRPO)-antibody conjugate for 1 hour at room temperature. The filter is again washed thoroughly with PBS and the antigen bands are identified by adding diaminobenzidine (DAB).

Enzyme assays, protein purification, and other classical biochemical methods are employed. DNA and RNA are analyzed by Southern blotting and Northern blotting techniques. Typically, the samples to be analyzed are size fractionated by gel electrophoresis. The samples, DNA or RNA, in the gels are then transferred to nitrocellulose or nylon membranes by blotting techniques. The blots, which are replicas of sample patterns in the gels, are hybridized with probes in Southern and Northern analysis. Specific bands of interest can then be visualized by detection systems such as autoradiography.

DNA can also be transferred using the DEAE-Dextran method of Kimura, et al. *Virology* 49:394 (1972) and Sompayrac, et al., *Proc. Natl. Acad. Sci.* USA 78:7575 (1981); the electroporation method of Potter, *Proc. Natl. Acad. Sci.* USA 81:7161 (1984), and the protoplast fusion method of Sandri-Goddin, et al. *Molec. Cell Biol.* 1:743 (1981).

Most preferably, transgenic shrimp are prepared by inserting recombinant DNA into newly fertilized shrimp oocytes either by microinjection or by "biolistic" bombardment in accordance with methods known to those skilled in the art.

The shrimp selection method described generally above will be further understood with reference to the following non-limiting examples.

EXAMPLE 1

Identification of Tandem Repeats in the *Penaeus vannamei* Genome by Gel Electrophoresis DNA isolated from *Penaeus vannamei* by chloroform extraction in the presence of cetyl trimethyl ammonium bromide, as described above, was tested for digestion with a set of eight restriction enzymes having six-base recognition sites. DNA was incubated with 10–20 enzyme units per reaction at 37° C. for 4–6 hours. The restriction enzymes were BamHI, ClaI, EagI, EcoRI, HindIII, KpnI, PstI, and XbaI. The results, shown in FIG. 2A, revealed the presence of at least two different kinds of repeated DNA sequence elements. Digestion with HindIII, KpnI and PstI all produced a prominent band of approximately 2.2 kilobase pairs. The appearance of the same band in three different digests is characteristic of a tandemly-repeated structure. Digestion with KpnI also produced a significant band at about 1.8 kilobase pairs. The absence of this band in any other lane suggests that it is derived from a repeat element that is dispersed in the genome.

A Southern blot of the electrophoretic gel shown in FIG. 2A was probed with pBSr3, a plasmid containing the 5.8 S rRNA gene, part of the 28 S rRNA gene, and part of the internal transcribed spacer region, all from *Artemia franciscana*. The results, shown in FIG. 2B, demonstrate cross-hybridization with the probe sequences. A second Southern blot of the electrophoretic gel with a plasmid containing histone genes from *Artemia franciscana* produced no signals, indicating a lack of hybridization.

Genomic DNA from *Penaeus vannamei* was also digested with ten restriction enzymes having four-base recognition sites. The restriction enzymes were A/uI, DdeI, HaeIII, HhaI, HinfI, HinPI, HpaII, MspI, Sau3AI, and EcoRI "star". These restriction enzymes cut the DNA molecule more frequently and produced smaller fragments. The results, shown in FIG. 3, revealed a third repeat element. Six different digests produced the same prominent band of about 620 base pairs. This plus the appearance of a probable dimer of about 1250 base pairs in the HaeIII digest indicate that this is a tandemly repeated sequence.

Figure 3:
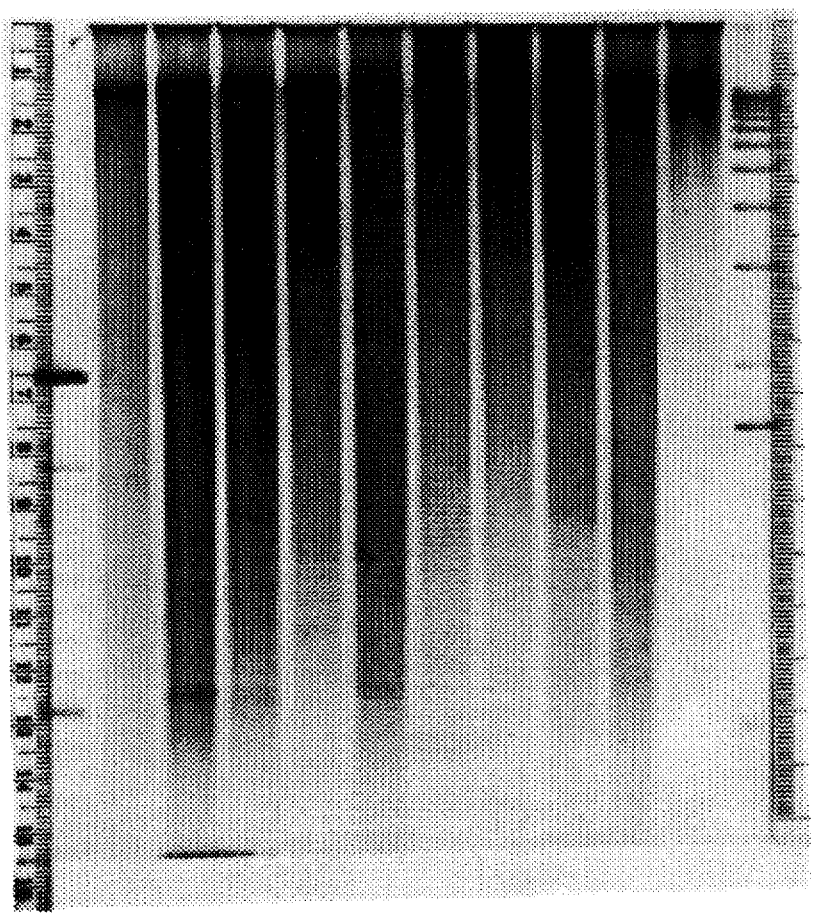
FIG. 3 is an agarose gel electrophoresis of DNA isolated from post-larvae Penaeus shrimp after digestion with A/uI (lane 1), DdeI (lane 2), HaeIII (lane 3), HhaI (lane 4), HinfI (lane 5), HinPI (lane 6), HpaII (lane 7), MspI (lane 8), Sau3AI (lane 9) and EcoRI "star" (lane 10). The lanes labelled "M" are markers.

The electrophoretic gel shown in FIG. 3 was Southern blotted with two different plasmids containing different parts of the ribosomal RNA genes of *Artemia franciscana*. The ribosomal RNA genes from the anostacan shrimp *Artemia franciscana* have been cloned and are described by Vaughn, et al., *Biochem and Biophys. Acta*, 697:156–161 (1982). The results, not shown, demonstrate cross-hybridization with these probes.

Figure 4:
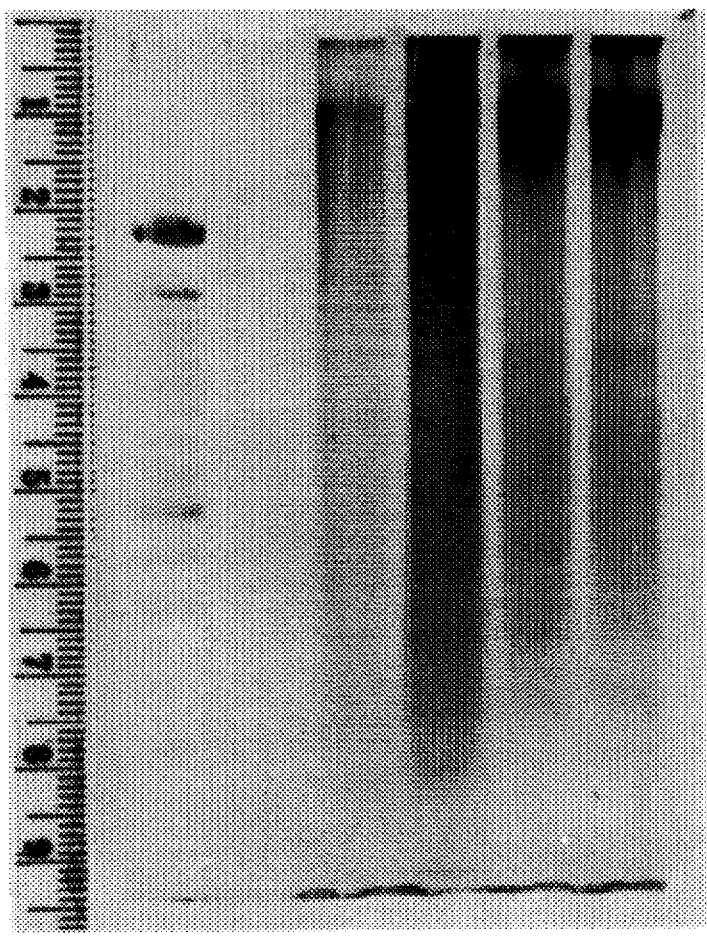
FIG. 4 is a gel electrophoresis of DNA isolated from post-larvae Penaeus shrimp after digestion with Sau3AI and fractionation on a low-melting agarose gel. The lane labelled "M" is a marker.

Penaeus DNA, isolated by the method described above, was digested with the restriction enzyme Sau3AI and fractionated on a low-melting agarose gel (SeaPlaque™, FMC Corporation, Rockland, Me.) for preparative gel electrophoresis. This restriction enzyme was chosen because fragment generated by digestion with Sau3AI can be directly cloned into the BamHI site of a vector. The results, shown in FIG. 4, revealed a fragment at less than 100 base pairs, a second fragment between 100 and 200 base pairs, and other fragments at intervals of 60–70 base pairs. This "ladder" effect is characteristic of a tandemly repeated sequence element.

EXAMPLE 2

Amplification of the Internal Transcribed Spacer Region of *Penaeus vannamei* rRNA Genes DNA primers used for amplification of the internal transcribed spacer region of the 18 S and 28 S ribosomal RNA genes of *Artemia franciscana* were incubated with *Penaeus vannamei* DNA isolated by the chloroform/cetyl trimethyl ammonium bromide extraction method described above. Amplification of these genes was chosen because the internal transcribed spacer region of the ribosomal RNA genes is a likely candidate for polymorphism. Amplification was achieved by PCR in accordance with methods described in *Current Protocols in Molecular Biology* (John Wiley and Sons, 1987).

Figure 5A:
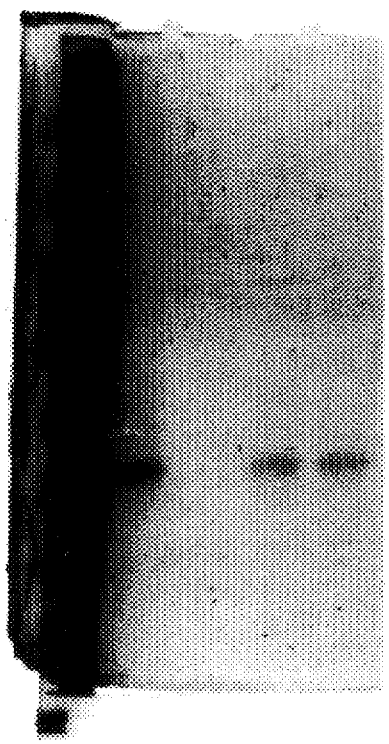
FIG. 5A is an electrophoretic gel of DNA amplified from 1 μl of Artemia DNA alone (lane 1) or in the presence of 1, 0.1, or 0.01 μl (lanes 2–4) of Penaeus DNA. DNA concentrations were approximately 0.1 mg/ml. Primers used were specific for the 18 S and 28 S ribosomal genes and positioned so as to amplify the internal transcribed spacer.
Figure 5B:
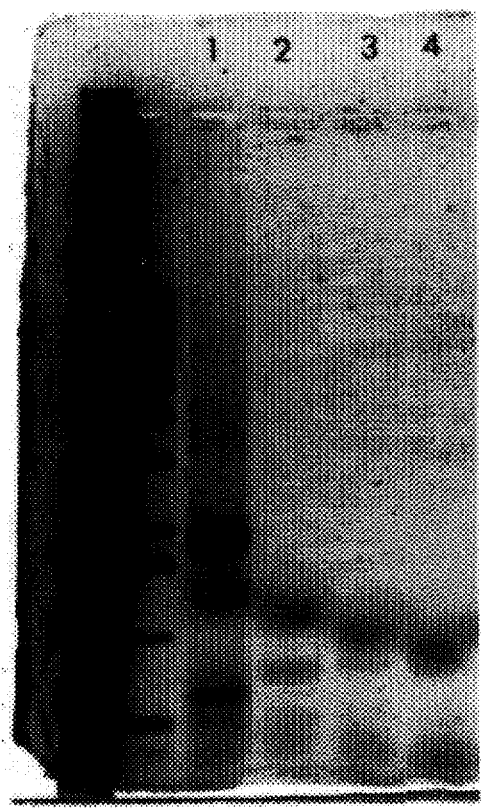
FIG. 5B is an electrophoretic gel of DNA amplified from 1 μl of Artemia DNA (lane 1) or from $10^{-2}$, $10^{-4}$, or $10^{-6}$ μl of Penaeus DNA using the polymerase chain reaction. DNA concentrations were approximately 0.1 mg/ml. Primers used were specific for the 18 S and 28 S ribosomal genes and positioned so as to amplify the internal transcribed spacer.

The DNA isolates contained an unknown substance that inhibited amplification. Inhibition was eliminated by diluting the Penaeus DNA sample ten fold or greater as shown in FIGS. 5A and 5B.

EXAMPLE 3

Attempted Isolation of Penaeus DNA Using the Autoextract™ System

Figure 6:
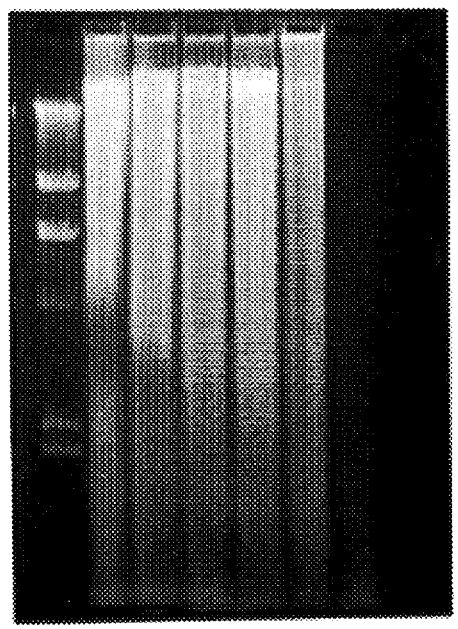
FIG. 6 is an elctrophoretic gel of an Autoextract™ preparation of Penaeus shrimp DNA.

An Autoextract™ system, purchased from Isogene Biotechnology, Inc. (Overland Park, Kans.) was used in an attempt to isolate DNA from a sample of Penaeus shrimp in accordance with the manufacturer's instructions. An agarose electrophoretic gel was prepared. Standard DNA molecular weight markers were loaded in the left lane. DNA from crude nuclei was loaded in lane 1 as a control. Lysate derived from the Autoextract™ procedure before (lane 2) and after (lane 3) incubation at 60° C. for two hours, and after phenol/chloroform extraction (lane 4) yielded badly fragmented DNA as shown in FIG. 6. Lane 5 of FIG. 6 represents DNA from a previously unsuccessful Autoextract™ attempt.

EXAMPLE 4

Attempted Isolation of Penaeus DNA Using the A.S.A.P.™ Kit

An A.S.A.P.™ kit, purchased from Boehringer Mannheim, (Indianapolis, Ind.) was used in accordance with the manufacturer's instructions in an attempt to isolate Penaeus DNA from a shrimp sample using a gel matrix method. An agarose electrophoretic gel was prepared. Standard DNA molecular weight markers were loaded in left lane. DNA isolated from post-larvae after enzyme digestion was loaded in lane 1, and DNA subjected to purification on the A.S.A.P.™ column was loaded in lane 2.

Figure 7:
FIG. 7 is an electrophoretic gel of an A.S.A.P.™ preparation of Penaeus shrimp DNA.

As shown in FIG. 7, the DNA subjected to the A.S.A.P.™ purification procedure was badly fragmented.

Modifications and variations of the present invention, a genetic method for selecting shrimp having favorable growth characteristics, and transgenic shrimp, will be obvious to those skilled in the art from the foregoing detailed description. Such modifications and variations are intended to come within the scope of the appended claims.

We claim:

1. A method of screening for Penaeus shrimp having a pre-determined genetically-transmitted characteristic associated with the presence of a genetic marker in a characteristic pattern in Penaeus shrimp comprising the steps of:
   a) isolating nuclear nucleic acid molecules from individual shrimp of the same species,
   b) hybridizing to the isolated nucleic acid molecules a labelled probe for a nucleic acid marker, which is variable among individuals of the same species, said marker selected from the group consisting of an internal transcribed spacer region of ribosomal RNA genes, a variable number tandem repeat, a restriction fragment length polymorphism in ribosomal RNA genes, and a dispersed repeat in ribosomal RNA genes; and,
   c) determining if the marker is present in the isolated DNA molecules in the characteristic pattern associated with the are determined genetically transmitted characteristic.

2. The method of claim 1 wherein the nucleic acid molecule is isolated by extraction with an organic solvent mixture comprising chloroform and cetyl trimethyl ammonium bromide.

3. The method of claim 1 comprising the additional steps of digesting the DNA with a restriction enzyme to produce restriction fragments and separating the restriction fragments by gel electrophoresis prior to the hybridization step.

4. The method of claim 1 wherein the probe is labelled with a radioactive label.

5. The method of claim 1 wherein the marker is a primer for amplification of a portion of the nuclear nucleic acid molecule.

6. The method of claim 5 comprising the additional step of amplifying the portion of the nuclear nucleic acid molecule before the selection step.

7. The method of claim 6 wherein the nucleic acid molecule is amplified by a technique selected from the group consisting of polymerase chain reaction, ligase amplification reaction, ligase hybridization, Qβ bacteriophage replicase, transcription-based amplification system, genomic amplification with transcript sequencing and nucleic acid sequence-based amplification.

8. The method of claim 1 wherein the shrimp are a species of shrimp selected from the group consisting of *Penaeus vannamei, Penaeus chinensis, Penaeus monodon, Penaeus stylirostris, Penaeus japonicus, Penaeus penicillatus, Penaeus merguiensis, Penaeus indicus, Penaeus subtilis, Penaeus paulensis, Penaeus setiferus, Penaeus brasiliensis, Penaeus duorarum, Penaeus occidentalis, Penaeus schmitti, Penaeus californiensis, Penaeus semisulcatus,* and *Penaeus latisulcatus.*

9. The method of claim 1 wherein the shrimp are of the species *Penaeus vannamei.*

10. The method of claim 7 wherein the polymerase chain reaction is the polymerase chain reaction in situ.

11. A method of screening for Metapenaeus shrimp having a predetermined genetically-transmitted characteristic associated with the presence of a genetic marker in a characteristic pattern in Metapenaeus shrimp comprising the steps of:
   a) isolating nuclear nucleic acid molecules from individual shrimp of the same species,
   b) hybridizing to the isolated nucleic acid molecules a labelled probe for a nucleic acid marker, which is variable among individuals of the same species, said marker selected from the group consisting of an internal transcribed spacer region of ribosomal RNA genes, a variable number tandem repeat, a restriction fragment length polymorphism in ribosomal RNA genes, and a dispersed repeat in ribosomal RNA genes; and,
   c) determining if the marker is present in the isolated DNA molecules in the characteristic pattern associated with the predetermined genetically-transmitted characteristic,
   wherein the Metapenaeus shrimp are selected from the group consisting of *Metapenaeus monoceros, Metapenaeus dobsoni, Metapenaeus affinis,* and *Metalaenaeus brivicomis.*

* * * * *